US00PP17791P3

(12) United States Plant Patent
Zary

(10) Patent No.: US PP17,791 P3
(45) Date of Patent: Jun. 5, 2007

(54) CLIMBER ROSE PLANT NAMED 'JACAMITE'

(50) Latin Name: *Rosa hybrida*
Varietal Denomination: JACamite

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 6 days.

(21) Appl. No.: 11/134,215

(22) Filed: May 19, 2005

(65) Prior Publication Data

US 2006/0265791 P1 Nov. 23, 2006

(51) Int. Cl.
*A01H 5/00* (2006.01)

(52) U.S. Cl. ..... Plt./115

(58) Field of Classification Search ..... Plt./115, Plt./139, 140, 108
See application file for complete search history.

*Primary Examiner*—Howard J. Locker
(74) *Attorney, Agent, or Firm*—Klarquist Sparkman LLP

(57) ABSTRACT

Climber rose plant having very large, hybrid tea form flowers in large clusters; continuous bloom during the growing season; very vigorous climbing habit; strong, sweet fragrance; disease resistant foliage and ability to grow vigorously on its own roots.

1 Drawing Sheet

Genus and species: *Rosa hybrida.*
Variety denomination: 'JACamite'.

ORIGIN OF THE INVENTION

The present invention relates to a new and distinct variety of a climber rose plant named 'JACamite' which was originated by me by crossing the variety 'JACsat' (Dynamite), U.S. Plant Pat. No. 8,741, with the variety 'JACpicl' (Dream Weaver), U.S. Plant Pat. No. 9,492.

BACKGROUND OF THE INVENTION

The primary objective of this breeding was to produce a new rose variety having the vigorous climbing habit and large flower size of the female parent combined with the clustering ability and repeat flowering of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Very large, hybrid tea form flowers in large clusters.
2. Continuous bloom during the growing season.
3. Very vigorous climbing habit.
4. Strong, sweet fragrance.
5. Disease resistant foliage.
6. Ability to grow vigorously on its own roots.

Asexual reproduction of this new variety by cuttings, as performed at Wasco, Calif., shows that the foregoing and all other characteristics and distinctions come true to form and are established and transmitted through succeeding propagations.

Comparison with Parents

'JACamite' has red flowers and more continuous flowering than the female parent 'JACsat' which has coral pink flowers. 'JACamite' differs from the male parent 'JACpicl' which also has coral pink flowers.

Comparison with Similar Variety

The subject variety most closely resembles the female parent 'JACsat' (Dynamite) but differs as noted above and 'JACamite' has more continuous bloom and is more fragrant.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACsat' (Dynamite), U.S. Plant Pat. No. 8,741.
*Pollen parent.*—'JACpicl' (Dream Weaver), U.S. Plant Pat. No. 9,492.

FLOWER

Observations were made of plants commencing of three years of age grown on their own roots in a garden environment at Somis, Calif.

Blooming habit: Continuous.

Bud:

*Size.*—About 2.5–3.0 cm long and 1.7–1.8 cm in diameter when the petals start to unfurl.

*Form.*—The bud form is long, pointed ovoid.

*Color.*—When sepals first divide, bud color is Red Group 45C. When half blown, the upper sides of the petals are close to Red Group 45C; and the lower sides of the petals are Red Group 53D.

*Sepals.*—Color: Upper surface: Green Group 138C, sometimes overlayed with Greyed-Purple Group 184C. Lower surface: Green Group 137C. Length: 25 mm. Width: 8–9 mm. Shape: Subulate. Surface texture: Upper surface: Coriaceous. Lower surface: Smooth. There are three normally appendaged sepals. There are two unappendaged sepals with serrated edges.

*Receptacle.*—Color: Green Group 137D. Shape: Funnel. Size: Medium, about 14 mm long×9 mm wide. Surface: Smooth.

*Peduncle.*—Length: Short, averaging about 5–6 cm long. Surface: Smooth to touch, occasional gland present. Color: Green Group 137C, sometimes with a reddish blush of Greyed-Red Group 182D. Strength: Stiff, erect.

Bloom:

*Size.*—Large. Average open diameter is about 12 cm.

*Borne.*—Several together in rounded clusters of 5–7 blooms.

*Stems.*—Strength: Strong. Average length is about 30–40 cm on laterals, 130–150 cm on new climbing canes with a diameter of 4–5 mm on laterals and 7–8 mm on main canes.

*Form.*—When first open: High centered. Permanence: Outer petals curl back.

*Petalage.*—Number of petals under normal conditions: 30–35.

*Color.*—The upper sides of the petals are close to Red Group 45C. The reverse sides of the petals are Red Group 53D. The base of the petal has a very small light yellow color spot 3 mm×3 mm of Yellow Group 2C. The major color on the upper side is close to Red Group 45C.

*Variegations.*—None observed.

*Discoloration.*—The general tonality at the end of the first day: No change. At the end of the third day: No change. Further aging: Little, if any change, until petal drop.

*Fragrance.*—Strong, sweet, fruity.

Petals:

*Texture.*—Thick.

*Shape.*—Round.

*Length.*—5.0–5.5 cm.

*Width.*—5.0 cm.

*Surface.*—Smooth.

*Margin.*—Entire.

*Apex shape.*—Rounded.

*Base shape.*—Rounded.

*Form.*—Tips slightly recurved.

*Arrangement.*—Imbricated.

*Petaloids.*—Number: 2–5. Size: 3–8 mm in length, 1–3 mm in width. Color: Red Group 45C.

*Persistence.*—Petals drop off cleanly before drying.

*Lastingness.*—On the plant: Long (about 6–7 days). As a cut flower: Long (about 8–9 days).

Reproductive parts:

*Stamens.*—Number: 80–90. Length: 9–11 mm. Anthers: Length: 3 mm. Color: Yellow-Orange Group 16D. Arrangement: Regular around styles. Filaments: Color: Yellow Group 5C. Length: 6–8 mm. Pollen: Color: Yellow-Orange Group 22B.

*Pistils.*—Number: 35–40. Length: 4–5 mm. Styles: Color: Yellow Group 2D. Length: 3–4 mm. Stigmas: Color: Yellow-White Group 158C. Length: 1 mm.

*Hips.*—Color: Orange Group N25A. Shape: Spherical. Size: 30–35 mm diameter, 30–35 mm top to bottom, 20–30 seeds inside hips. Seed Shape: Typical achene. Seed Size: Diameter: 1–2 mm. Length: 2–3 mm.

PLANT

Form: Climber.

Growth: Very vigorous.

Age at maturity: 3 years.

Mature plant: Height: 4 meters. Width: 3 meters.

*Rootstock.*—Own roots.

Foliage: Number of leaflets on normal mid-stem leaves: 5 or 7.

*Size.*—Large. About 16 cm long×12 cm wide.

*Quantity.*—Abundant.

*Color.*—New foliage: Upper side: Greyed-Red Group 178A. Lower side: Greyed-Red Group 178B. Old foliage: Upper side: Green Group 137A. Lower side: Green Group 137D.

Leaflets:

*Size.*—About 55–58 mm long×30–33 mm wide.

*Shape.*—Pointed oval.

*Base shape.*—Aequilateral.

*Apex shape.*—Acuminate.

*Texture.*—Leathery, glossy.

*Edge.*—Serrated.

*Serrations.*—Single.

*Petiole.*—Color: Yellow-Green Group 146D.

*Petiole rachis.*—Color: Yellow-Green Group 146D. Underside: Rough with prickles.

*Auricles.*—None.

*Stipules.*—Length: 20–23 mm, edges smooth but a few glands are present; not serrated. Shape: Adnate with middle part narrowing and margin comb-shaped. Color: Green Group 138C.

*Disease resistance.*—Resistant to mildew and rust and susceptible to blackspot under normal growing conditions.

*Pest resistance.*—Not observed.

*Vein color.*—Yellow-Green Group 146D.

*Venation pattern.*—Reticulate.

Wood:

*New wood.*—Color: Yellow-Green Group 146C often overlain with Greyed-Red Group 178B. Bark: Smooth.

*Old wood.*—Color: Yellow-Green Group 146C. Bark: Smooth.

Prickles:

*Quantity.*—On main canes from base: 18–21 per 15 cm. On laterals from main canes: 18–21 per 15 cm.

*Form.*—Hooked downward.

*Length.*—7–9 mm.

*Color when young.*—Greyed-Red Group 178A.

*Color when mature.*—Greyed-Orange Group N170B.

Small prickles:

*Quantity.*—On main stalks: None. On laterals: None.

Winter hardiness: Hardy to Zone 5.

I claim:

1. A new and distinct variety of rose plant of the climber class, substantially as herein shown and described, characterized particularly by its very large hybrid tea form red flowers in large clusters; continuous bloom during the growing season; very vigorous climbing habit; strong, sweet fragrance; disease resistant foliage and ability to grow vigorously on its own roots.

* * * * *

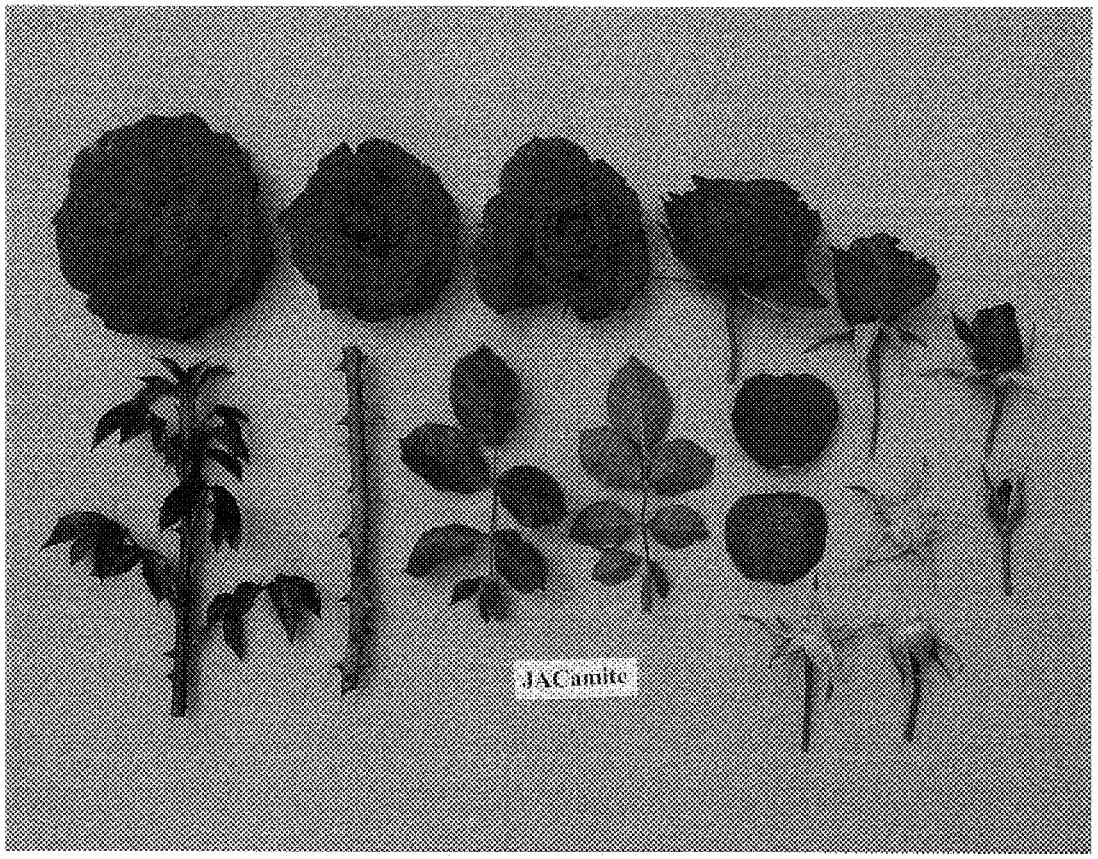
JACanute